US007838025B2

(12) United States Patent
Koenig et al.

(10) Patent No.: US 7,838,025 B2
(45) Date of Patent: Nov. 23, 2010

(54) PRODUCTS AND METHODS FOR MAINTAINING OR INCREASING CERAMIDE LEVELS IN SKIN

(75) Inventors: David W. Koenig, Menasha, WI (US); Jamie Joseph Van Gompel, Madison, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 12/254,956

(22) Filed: Oct. 21, 2008

(65) Prior Publication Data

US 2009/0053286 A1 Feb. 26, 2009

Related U.S. Application Data

(62) Division of application No. 10/229,161, filed on Nov. 19, 2002, now Pat. No. 7,585,518.

(51) Int. Cl.
A61K 35/72 (2006.01)
A61K 35/80 (2006.01)
A61K 9/70 (2006.01)
A61K 35/78 (2006.01)

(52) U.S. Cl. ............. 424/443; 424/195.16; 424/195.17; 424/728; 424/729; 424/750

(58) Field of Classification Search ........................ None
See application file for complete search history.

(56) References Cited

U.S. PATENT DOCUMENTS

| | | | |
|---|---|---|---|
| 4,100,324 A | 7/1978 | Anderson et al. |
| 4,609,547 A | 9/1986 | Garman et al. |
| 5,141,803 A | 8/1992 | Pregozen |
| 5,152,996 A | 10/1992 | Corey et al. |
| 5,215,759 A | 6/1993 | Mausner |
| 5,472,700 A | 12/1995 | Staetz et al. |
| 5,512,283 A | 4/1996 | Byers et al. |
| 5,601,833 A | 2/1997 | Ribier et al. |
| 5,648,083 A | 7/1997 | Blieszner et al. |
| 5,723,138 A | 3/1998 | Bae et al. |
| 5,804,168 A | 9/1998 | Murad |
| 5,830,916 A | 11/1998 | Hannun et al. |
| 5,851,782 A | 12/1998 | Hannun et al. |
| 5,888,524 A | 3/1999 | Cole |
| 5,906,992 A | 5/1999 | Fonsny et al. |
| 5,916,573 A | 6/1999 | Spiers et al. |
| 5,935,596 A | 8/1999 | Crotty et al. |
| 5,985,300 A | 11/1999 | Crotty et al. |
| 5,993,857 A | 11/1999 | Menzel et al. |
| 6,028,018 A | 2/2000 | Amundson et al. |
| 6,060,075 A | 5/2000 | Rao et al. |
| 6,117,440 A | 9/2000 | Suh et al. |
| 6,149,934 A | 11/2000 | Krzysik et al. |
| 6,159,487 A | 12/2000 | Znaiden et al. |
| 6,174,519 B1 | 1/2001 | Greene |
| 6,187,728 B1 | 2/2001 | McManus |
| 6,235,272 B1 | 5/2001 | Greene |
| 6,235,737 B1 | 5/2001 | Styczynski et al. |
| 6,258,355 B1 | 7/2001 | Cavaliere widow Vesely et al. |
| 6,280,751 B1 | 8/2001 | Fletcher et al. |
| 6,338,855 B1 | 1/2002 | Albacarys et al. |
| 6,531,132 B1 | 3/2003 | Paufique |
| 6,656,168 B2 | 12/2003 | Braverman et al. |
| 2002/0015743 A1 | 2/2002 | Meybeck et al. |
| 2002/0022043 A1 | 2/2002 | Miller |
| 2002/0136755 A1 | 9/2002 | Tyrrell et al. |
| 2002/0150610 A1 | 10/2002 | Kono et al. |

FOREIGN PATENT DOCUMENTS

| | | |
|---|---|---|
| AU | 730197 B2 | 3/2001 |
| CN | 1071844 A | 5/1993 |
| CN | 1280008 A | 1/2001 |
| DE | 19824680 A | 12/1999 |
| DE | 19824683 A | 12/1999 |
| DE | 19824727 A | 12/1999 |
| DE | 19827624 A1 | 12/1999 |
| EP | 350275 A2 | 1/1990 |
| EP | 870507 A1 | 10/1998 |

(Continued)

OTHER PUBLICATIONS

Di Marzio et al. "Effect of the Lactic Acid Bacteria *Streptococcus thermophilus* on Ceramide Levels in Human Keratinocytes in Vitro and Stratum Corneum in Vivo" Soc. Invest. Derm., 113(1):98-106 (1999).

(Continued)

*Primary Examiner*—Christopher R Tate
*Assistant Examiner*—Randall Winston
(74) *Attorney, Agent, or Firm*—Armstrong Teasdale LLP

(57) ABSTRACT

Disclosed are methods and products such as wet wipes and absorbents capable of providing a skin health benefit when utilized in the intended fashion. More specifically, the products described herein comprise an agent, such as a botanical extract, which is capable of increasing the activity of sphingomyelinase according to a Sphingomyelinase Activity Screening Test and/or decreasing the activity of ceramidase according to a Ceramidase Activity Screening Test. By increasing the activity of sphingomyelinase and/or decreasing the activity of ceramidase, the agents in combination with the products described herein are able to maintain or increase the level of ceramides in the skin leading to improved skin health.

16 Claims, No Drawings

FOREIGN PATENT DOCUMENTS

| | | |
|---|---:|---|
| EP | 993822 A1 | 4/2000 |
| GB | 2363074 A | 12/2001 |
| JP | 59166585 A | 9/1984 |
| JP | 61115013 A | 6/1986 |
| JP | 1207339 A | 8/1989 |
| JP | 3029623 A | 2/1991 |
| JP | 3236311 A | 10/1991 |
| JP | 7228892 A | 8/1995 |
| JP | 8217658 A | 8/1996 |
| JP | 8268859 A | 10/1996 |
| JP | 8294395 A | 11/1996 |
| JP | 9040523 A | 2/1997 |
| JP | 9110615 A | 4/1997 |
| JP | 9194317 A | 7/1997 |
| JP | 11116417 A | 4/1999 |
| JP | 11130627 A | 5/1999 |
| JP | 11139959 A | 5/1999 |
| JP | 11228325 A | 8/1999 |
| JP | 11292710 A | 10/1999 |
| JP | 11332778 A | 12/1999 |
| JP | 2000053533 A | 2/2000 |
| JP | 2000053923 A | 2/2000 |
| JP | 2000063262 A | 2/2000 |
| JP | 2000070097 A | 3/2000 |
| JP | 2000169359 A | 6/2000 |
| JP | 2001009950 A | 1/2001 |
| JP | 2001261543 A | 9/2001 |
| KR | 9708991 B1 | 6/1997 |
| WO | 9622015 A1 | 7/1996 |
| WO | 9803147 A1 | 1/1998 |
| WO | 9836640 A1 | 8/1998 |
| WO | 9842303 A1 | 10/1998 |
| WO | 9907220 A1 | 2/1999 |
| WO | 9915208 A2 | 4/1999 |
| WO | 9936032 A1 | 7/1999 |
| WO | 9953763 A1 | 10/1999 |
| WO | 9962478 A1 | 12/1999 |
| WO | 9966897 A1 | 12/1999 |
| WO | 0032162 A1 | 6/2000 |
| WO | 0044344 A2 | 8/2000 |
| WO | 0100033 A1 | 1/2001 |
| WO | 0100253 A1 | 1/2001 |
| WO | 0101949 A1 | 1/2001 |
| WO | 0119325 A1 | 3/2001 |
| WO | 0126617 A1 | 4/2001 |
| WO | 0176371 A1 | 10/2001 |
| WO | 0183666 A2 | 11/2001 |
| WO | 0195728 A1 | 12/2001 |

OTHER PUBLICATIONS

Higaki et al. "*Staphylococcus* Species on the Skin Surface of Infant Atopic Dermititis Patients" J. Inter. Med. Res., 26:98-101 (1998).

Jin et al. "Analysis of beta-glucocerebrosidase and Ceramidase Activities in Atopic and Aged Dry Skin" Acta. Derm. Venerol., 74:337-340 (1994).

Marekov et al. "Cermides are Bound to Structural Proteins of the Human Foreskin Epidermal Cornfield Cell Envelope" J. Biol. Chem., 273(28):17763-17770 (1998).

Okino et al. "Purification and Characterization of a Novel Ceramidase from *Pseudomonas aeruginosa*" J. Biol. Chem., 272(23):14368-14373 (1998).

PCT Invitation to Pay Additional Fees from PCT/US03/13489, dated Sep. 23, 2003.

Official Letter from EP 03721964.9, dated Dec. 13, 2007.

Extended European Search Report from European Application No. 08004528.9, dated Jun. 6, 2008.

Non-Final Office action from U.S. Appl. No. 10/299,161, dated Oct. 3, 2005.

Non-Final Office action from U.S. Appl. No. 10/299,161, dated Mar. 23, 2006.

Final Office action from U.S. Appl. No. 10/299,161, dated Sep. 12, 2006.

Non-Final Office action from U.S. Appl. No. 10/299,161, dated Jan. 18, 2007.

Non-Final Office action from U.S. Appl. No. 10/299,161, dated Jul. 9, 2007.

Final Office action from U.S. Appl. No. 10/299,161, dated Jan. 11, 2008.

European Office Action regarding European Application No. 08004528.9, dated Sep. 11, 2009.

Printout of http://www.chemidex.com/en/NA/PCC/Detail/3030/91296/DRAGODERM%C2%AE-NO-118726, printed Mar. 26, 2010.

Printout of http://laboratorium-as.pl/oferta/pinfo/118726.PDF?PHPSESSID=254caf10206d8099b7215936a768c216, printed Mar. 26, 2010.

Printout of Dragoderm 118726 Active Ingredients from Symrise, available at http://www.symrise.com/fileadmin/user_upload/pdf/Dragoderm_A4.pdf, printed Jun. 1, 2010.

PRODUCTS AND METHODS FOR MAINTAINING OR INCREASING CERAMIDE LEVELS IN SKIN

CROSS REFERENCE TO RELATED APPLICATION

This patent application is a divisional application of U.S. patent application Ser. No. 10/299,161 filed on Nov. 19, 2002.

BACKGROUND OF THE INVENTION

The present invention relates to products and methods for maintaining or increasing the intracellular concentration of ceramides. More particularly, the present invention relates to the use of certain agents, such as botanical extracts, in wipes and absorbent products to maintain or increase intracellular ceramide concentrations. Intracellular ceramide concentrations are maintained or increased in the present invention by introducing one or more agents capable of increasing the activity of sphingomyelinase and/or decreasing the activity of ceramidase.

Ceramide (N-acylsphingosine) is a lipid metabolite and is an important intracellular messenger which is released inside a cell within a few hours of stimulation with various agents. Ceramide is regarded as a second messenger in the context of the sphingomyelin signal transduction pathway, and fulfills an important role in the moisturizing mechanism and barrier mechanism of skin. Ceramides are released by sphingomyelin as a result of the enzymatic effect of sphingomyelinases, which are forms of phospholipase C specific for sphingomyelin. Inside the cells, ceramide can influence growth and differentiation, regulate protein secretion, induce DNA fragmentation and apoptosis, and increase the synthesis and secretion of cytokines. Hydrolysis of sphingomyelin occurs rapidly after exposure of the cells to exogenous sphingomyelinase or to agonists which activate endogenous sphingomyelinases.

The importance of ceramides in the skin metabolism and health is well documented. The main cellular constituents of the epidermis are keratinocytes, melanocytes, Langerhans cells, fibroblasts, endothelial cells and macrophages. The intracellular space consists mainly of neutral lipids, glycoproteins, protein degradation products, desmosomes, active enzymes, products of sebaceous glands, and ceramides. As long as this brick and mortar structure is intact, the skin is endowed with both a protective layer and a selectively permeable filter.

During the differentiation process of the epidermis, which starts with cell division in the basal layer and ends with the death of keratinocytes and the development of the lipid barrier, the cells modify their lipid synthesis capability. The result is that the basal layer of the epidermis is characterized by phospholipids and cholesterol, whereas the outermost layer is characterized by cholesterol, free fatty acids and ceramides. The lipids of the horny layer, the main component of which consists of sphingolipids, play a crucial role in maintaining the permeability barrier of the epidermis to water. The sphingolipids are exuded from the lamellar bodies of the granular cells of the epidermis. Ceramides, which make up almost 50% of the horny layer of skin, are the main polar lipids of the horny layer and play a fundamental role in the barrier function of the skin against water leakage in cell adhesion and in the differentiation of the epidermis, as mentioned above.

Like the appearance of the surface of the skin, its functional properties also undergo changes with aging. Aging skin is characterized by a reduced water content in the horny layer associated with reduced transdermal leakage of water. It has been shown that ceramide concentration decreases with age, and this decrease may be responsible for the dehydration of the skin which is observed in the course of aging. In addition, abnormal ceramide levels (deficiencies) have been detected in atopic eczema, dermatosis and dermatitis, atopic dermatitis and psoriasis.

In addition to age, other external factors can reduce the amount of ceramides present in the skin and lead to skin irritation problems. For example, the enzyme ceramidase can degrade ceramides to sphingosine and free fatty acids upon contact with ceramides. Ceramidase is present in skin in certain layers where it performs a beneficial conversion function. However, when ceramidase is introduced onto skin from an external source such as bacteria (bacterial ceramidases) present in feces or nasal secretions, the ceramidase can degrade ceramides as mentioned above thereby reducing the intracellular concentration of ceramides and leading to dry, cracked skin.

In light of the foregoing, it is useful to maintain high levels of ceramides in the skin to maintain and promote healthy skin. As such, it would be advantageous to produce personal care products, such as wet wipes and absorbent care products, capable of maintaining or increasing the levels of ceramides in the skin. Because controlling the ceramide levels in the skin by the addition of natural ceramides is not practical due to the enormous expense of the purified lipid, there continues to be a need for economical products containing agents capable of maintaining or increasing the levels of ceramides in the skin.

SUMMARY OF THE INVENTION

The present invention relates to products and methods for improving skin health by maintaining or increasing the concentration of intracellular ceramides. More specifically, the present invention relates to products such as wet wipes and absorbent articles containing agents which are capable of improving the health of skin they contact during normal usage by maintaining or increasing the intracellular concentration of ceramides through various mechanisms.

The products of the present invention may comprise an agent, such as a botanical extract, for increasing sphingomyelinase activity for the production of ceramides by at least about 100%. In one embodiment, the sphingomyelinase activity increasing agent increases sphingomyelinase activity by at least about 100% as determined by a SAST Sphingomyelinase Activity Screening Test set forth herein. Because sphingomyelinase activity is required for the production of intracellular ceramides, an increase in such enzymatic activity results in increased ceramide levels. Furthermore, the products of the present invention may comprise a ceramidase activity decreasing agent for decreasing ceramidase activity by at least about 50%. In one embodiment, the ceramidase activity decreasing agent decreases ceramidase activity by at least about 50% as determined by a CAST Ceramidase Activity Screening Test set forth herein. Because ceramidases, such as bacterial ceramidases present on the skin, can degrade ceramides, a reduction in ceramidase activity reduces the amount of ceramides destroyed. By significantly increasing sphingomyelinase activity and/or decreasing ceramidase activity, the agents described herein significantly improve the health of skin by maintaining or increasing the level of ceramides in the skin.

Briefly, therefore, the present invention is directed to a wipe for improving skin health comprising a fibrous wipe substrate and a sphingomyelinase activity increasing agent for increasing sphingomyelinase activity for the production of ceramides by at least about 100%.

The present invention is further directed to a wipe for improving skin health comprising a fibrous wipe substrate and a ceramidase activity decreasing agent for decreasing ceramidase activity by at least about 50%.

The present invention is further directed to a wipe comprising a fibrous wipe substrate and a sphingomyelinase activity increasing agent for increasing sphingomyelinase activity for the production of ceramides by at least about 100% and a ceramidase activity decreasing agent for decreasing ceramidase activity by at least about 50%.

The present invention is further directed to a method for increasing the intracellular concentration of ceramides. The method comprises contacting skin with a sphingomyelinase activity increasing agent for increasing sphingomyelinase activity for the production of ceramides by at least about 100%.

Other objects and features of this invention will be in part apparent and in part pointed out hereinafter.

DETAILED DESCRIPTION OF THE PREFERRED EMBODIMENTS

In accordance with the present invention, it has been discovered that certain agents, such as certain botanical extracts, can be utilized in common products to maintain or increase the concentration of ceramides in skin and thereby improve skin health. Some of the agents described herein are capable of increasing sphingomyelinase activity by at least about 100% according to a SAST Sphingomyelinase Activity Screening Test set forth herein. By significantly increasing sphingomyelinase activity, the rate at which ceramides are produced is increased leading to a higher intracellular concentration of ceramides. Additionally or alternatively, the personal care products of the present invention can also improve the health of skin by comprising an agent capable of decreasing ceramidase activity by at least about 50% according to a CAST Ceramidase Activity Screening Test set forth herein. By reducing the activity of ceramidase at or near the skin surface, the level of destruction of ceramides is reduced resulting in a higher concentration of active ceramide compounds. Furthermore, it has been discovered that certain organic and inorganic cofactors can be used in combination with one or more of the agents described herein to provide additional benefits to the skin by further stimulating sphingomyelinase to increase the production of ceramides.

The personal care products of the present invention contain at least one agent, such as a botanical extract, which is capable of improving the health of skin contacted by the personal care product during normal use. Numerous personal care products can be used with the agents described herein in accordance with the present invention to improve the skin of the user. For example, one or more of the agents and/or cofactors described herein can be used in combination with wipes, such as wet wipes, hand wipes, face wipes, cosmetic wipes, household wipes, industrial wipes, dry wipes and the like, to improve the health of the skin by maintaining or increasing the ceramide level therein. Materials suitable for the substrate of the wipe are well known to those skilled in the art, and are typically made from a fibrous sheet material which may be either woven or nonwoven. For example, the wipes incorporating the agents described herein to improve skin health may include nonwoven fibrous sheet materials which include meltblown, coform, air-laid, bonded-carded web materials, hydroentangled materials, and combinations thereof. Such materials can be comprised of synthetic or natural fibers, or a combination thereof. Typically, wipes define a basis weight of from about 25 to about 120 grams per square meter and desirably from about 40 to about 90 grams per square meter.

In a particular embodiment, the wipes incorporating the agents described herein comprise a coform basesheet of polymeric microfibers and cellulosic fibers having a basis weight of from about 60 to about 80 grams per square meter and desirably about 75 grams per square meter. Such coform basesheets are manufactured generally as described in U.S. Pat. No. 4,100,324, which is incorporated by reference. Typically, such coform basesheets comprise a gas-formed matrix of thermoplastic polymeric meltblown microfibers, such as, for example, polypropylene microfibers, and cellulosic fibers, such as, for example, wood pulp fibers.

The relative percentages of the polymeric microfibers and cellulosic fibers in the coform basesheet can vary over a wide range depending upon the desired characteristics of the wet wipes. For example, the coform basesheet may comprise from about 20 to about 100 weight percent, desirably from about 20 to about 60 weight percent, and more desirably from about 30 to about 40 weight percent of the polymeric microfibers based on the dry weight of the coform basesheet being used to provide the wipes.

Alternatively, the wipes incorporating the agents described herein comprise a composite which includes multiple layers of materials. For example, the wipes may include a three-layer composite which includes an elastomeric film or meltblown layer between two coform layers as described above. In such a configuration, the coform layers may define a basis weight of from about 15 to about 30 grams per square meter and the elastomeric layer may include a film material such as a polyethylene metallocene film.

As mentioned above, one type of wipe suitable for use in combination with the agents described herein to improve skin health include wet wipes which contain a liquid solution or formulation. The amount of solution contained within each wet wipe may vary depending upon the type of material being used to provide the wet wipe, the type of solution being used, the type of container being used to store the wet wipes, and the desired end use of the wet wipes. Generally, each wet wipe can contain from about 150 to about 600 weight percent and desirably from about 250 to about 450 weight percent solution based on the dry weight of the wipe for improved wiping. In a particular aspect, wherein the wet wipes are made from a coform material comprising from about 30 to about 40 weight percent polymeric microfibers based on the dry weight of the wipe, the amount of solution contained within the wet wipe is from about 300 to about 400 weight percent and desirably about 330 weight percent based on the dry weight of the wet wipe. If the amount of solution is less than the above-identified range, the wet wipe may be too dry and may not adequately perform. If the amount of solution is greater than the above-identified range, the wet wipe may be oversaturated and soggy and the solution may pool in the bottom of the container holding the wet wipes.

In another embodiment, the personal care products which comprise one or more of the agents described herein for improving skin health can include absorbent personal care products such as diapers, training pants, adult incontinence garments, feminine napkins, paper towels, tampons, breast pads, interlabial pads, facial tissue, wound management products, and bath tissue. Such absorbent products are commonly utilized for absorbing various fluids including bodily fluids such as blood, menses, nasal secretions, feces, and urine. Materials and methods for making such absorbent products are well known to those skilled in the art. When utilized in their intended manner, the absorbent personal care products including the agent or agents described herein contact the skin such that the agent can interact with the naturally occurring skin compounds and improve the health of the skin.

In one embodiment of the present invention, an agent capable of increasing the activity of the enzyme sphingomyelinase is introduced into or onto a personal care product to improve the health of skin contacted by the personal care product by increasing ceramide production in the skin via the pathway described above. As previously mentioned, sphingomyelinase is an enzyme which hydrolyses the lipid sphingomyelin, a phospholipid component of cell membranes, to produce ceramide. As used herein the phrase "increasing the activity of the enzyme sphingomyelinase" and similar phrases mean that the enzymatic activity of sphingomyelinase on sphingomyelin is increased in the presence of the agent, as compared to the activity of sphingomyelinase on sphingomyelin in the absence of the agent. By introducing one or more of the agents described herein into or onto a personal care product, the agent(s) contacts the skin during use and can interact with the naturally occurring sphingomyelinase to increase the sphingomyelinase activity. In addition to interacting with naturally occurring sphingomyelinase, the agent can also interact with sphingomyelinase which may be present in exudates, such as feces or nasal secretions, to facilitate ceramide production at or near the skin surface. The increased sphingomyelinase activity results in an increased hydrolysis of sphingomyelin and the production of ceramides through in situ reactions on or near the skin surface, which is beneficial and improves skin health as discussed above.

Preferably, the agent, or combination of agents introduced into or onto the personal care product, is capable of increasing sphingomyelinase activity by at least about 100%, more preferably at least about 200%, still more preferably at least about 300%, and most preferably at least about 400%, as compared to the sphingomyelinase activity in the absence of the agent. In one embodiment, the agent or combination of agents introduced into or onto the personal care product, is capable of increasing sphingomyelinase activity by at least about 100%, more preferably at least about 200%, still more preferably at least about 300%, and most preferably at least about 400% as determined by a SAST Sphingomyelinase Activity Screening Test set forth herein. Such increases in sphingomyelinase activity can result in increased intracellular and extracellular levels of ceramides, which improves skin health. The sphingomyelinase activity increasing agent is preferably for increasing sphingomyelinase activity by at least about 100% as noted above. While this is the purpose and capability of the agent under many circumstances, it is noted that under certain conditions of application and skin condition, the actual increase in activity experienced on the skin may be other than at least about 100% even though the agent is for increasing such activity by at least about 100%.

SAST Sphingomyelinase Activity Screening Test

Agents, such as botanical extracts and related compounds, for example, are tested for their ability to increase the activity of sphingomyelinase in a sphingomyelinase/sphingomyelin-containing system. An increase in the activity of sphingomyelinase results in an increase in the hydrolysis of sphingomyelin and an increased production of ceramide. The Sphingomyelinase Activity Screening Test to determine the efficacy of an agent is completed as follows:

Preparation of Testing Solutions:

Step 1: Preparation of Testing Solution Comprising Sphingomyelinase, Sphingomyelin, and Agent: Combine the following to prepare a 100 microliter test solution: (1) 10 microliters of agent (such as a botanical extract, for example) where the agent is an aqueous solution or oil (if the agent is a powder or solid, prepare 10 microliters of a 0.1 microgram/milliliter solution by dissolving the appropriate amount of powder or solid in Phosphate Buffered Saline, pH=7.4); (2) 10 microliters of a 0.1 microgram/milliliter sphingomyelinase (Catalogue No. S7651, Sigma Chemical, St. Louis, Mo. (or equivalent)) in Phosphate Buffered Saline, pH=7.4, solution; (3) 10 microliters of a 250 microgram/milliliter BODIPY FL C5-Sphingomyelin (Molecular Probes, Eugene, Oreg. (or equivalent)) in Phosphate Buffered Saline, pH=7.4, solution; and (4) 70 microliters of Phosphate Buffered Saline, pH=7.4.

Step 2: Preparation of Control Testing Solution Comprising Sphingomyelinase and Sphingomyelin: Combine the following to prepare a 100 microliter test solution: (1) 10 microliters of a 0.1 microgram/milliliter sphingomyelinase in Phosphate Buffered Saline, pH=7.4, solution; (2) 10 microliters of a 250 microgram/milliliter BODIPY FL C5-Sphingomyelin in Phosphate Buffered Saline, pH=7.4, solution; and (3) 80 microliters of Phosphate Buffered Saline, pH=7.4.

Step 3: Preparation of Control Testing Solution Comprising Sphingomyelin: Combine the following to prepare a 100 microliter test solution: (1) 10 microliters of a 250 microgram/milliliter BODIPY FL C5 Sphingomyelin in Phosphate Buffered Saline, pH=7.4, solution; and (2) 90 microliters of Phosphate Buffered Saline, pH=7.4.

Step 4: Preparation of Control Testing Solution Comprising Agent and Sphingomyelin: Combine the following to prepare a 100 microliter test solution: (1) 10 microliters of agent where the agent is an aqueous solution or oil (if the agent is a powder or solid, prepare 10 microliters of a 0.1 microgram/milliliter solution by dissolving the appropriate amount of powder or solid in Phosphate Buffered Saline, pH=7.4); (2) 10 microliters of a 250 microgram/milliliter BODIPY FL C5 Sphingomyelin in Phosphate Buffered Saline, pH=7.4, solution; and (3) 80 microliters of Phosphate Buffered Saline, pH=7.4.

Assay:

Step 1: Shake each of the four test solutions for 30 minutes on a laboratory shaker (e.g. S/P Vortrex-Genie; Deerfield, Ill. at a setting of about 6) at 25° C. to thoroughly mix each testing solution and allow chemical interaction and reaction between the testing mixture components.

Step 2: Add 1 milliliter of a 2:1 (by volume) mixture of chloroform:methanol to each testing solution to stop the chemical reactions. After the addition of the chloroform:methanol mixture, each testing solution is vortexed (e.g. S/P Vortrex-Genie; Deerfield, Ill. at a setting of about 6) for a period of time of about 1 minute to ensure that the chloroform:methanol mixture is thoroughly distributed throughout the testing mixture.

Step 3: Remove 0.8 milliliters of solution from the organic phase of each testing solution and introduce the removed solution into a thin layer chromatography vial for further analysis.

Thin Layer Chromatography Procedure:

Step 1: Introduce 5 microliters of a testing solution onto a thin layer chromatography plate, such as a high performance thin layer chromatography silica gel 60 plate (MERCK, Damstady, Germany), or similar plate. The spotting of the testing solution onto the plate may be done with a CAMAG Auto TLC Sampler 4 (Muttenz, Switzerland) for example, or similar device.

Step 2: Develop each testing solution by introducing a 90:20:0.5 (by volume) chloroform:methanol:ammonium hydroxide mixture onto each plate and allowing the mixture to run to a length of 8 centimeters.

Step 3: Quantify the fluorescent cleavage products on the thin layer chromatography plates by image analysis using an Alpha Innotech Flourchem Plate Imaging System (San Leandro, Calif.), or similar system. Each plate typically contains a maximum of ten test samples, three positive control samples (substrate and sphingomylenase) and one negative control sample (substrate and no enzyme). The plates were imaged by illuminating with a UV light source (364 nm) and a digital image was taken through a 585 nm barrier filter with the Flourchem Imager. All fluorescent bands are analyzed using the Flourchem image analysis software and the brightness for each band determined. The Flourchem software determined the Integrated Density Value (IDV) and the Area (pixels) for each fluorescent band. From this information, a Brightness value is calculated by the Fluorchem software. The following calculation is used:

Brightness=IDV/AREA where the IDV is the sum of all of the pixel values, AREA is the size (in pixels) of the region enclosed by a box of 2000-2500 pixels in size. To calculate the effect of the compounds on enzyme activity, the negative control brightness is first subtracted from all of the samples. Then the test compound band on a plate is divided by the average value of the three positive control bands for the same plate. A value above 1 indicates a sphingmyelinase enhancer, a value below 1 indicates an inhibitor.

Suitable agents for use in combination with the personal care products described herein to increase the activity of sphingomyelinase by at least about 100% to ultimately produce an increased amount of intracellular ceramides include both botanical extracts and other compounds. Specifically, it has been found that the following agents increase sphingomyelinase activity as determined by the Sphingomyelinase Activity Screening Test described herein by at least about 100% and are suitable for use in accordance with the present invention: Sedaplant Richter, Chlorella, Hexaplant Richter, Lavender, Marigold (Calendula), Gotu Kola PE 4:1, Spirulina, Chamonile CL, Harpagophytum (Devil's Claw), Dragoderm, Phytoplenolin, Aloe Ferox HS, Sea Parsley Extract, Butcher's Broom HS, American Ginseng, Microat afa Complex, and Actiphyte of Japanese Green Tea Conc. Preferred agents are Chlorella, Lavender, Spirulina, Dragoderm, Phytoplenolin, Aloe Ferox HS, and American Ginseng.

When present on a dry wipe substrate or on an absorbent product, the agent for increasing the activity of sphingomyelinase is present in an amount of from about 0.01% (by weight of the treated substrate or product) to about 50% (by weight of the treated substrate or product), preferably from about 0.01% (by weight of the treated substrate or product) to about 10% (by weight of the treated substrate or product). When present as part of the liquid formulation of a wet wipe, the agent is present in an amount of from about 0.01% (by total weight of the liquid formulation) to about 50% (by total weight of the liquid formulation), more preferably from about 0.01% (by total weight of the liquid formulation) to about 10% (by total weight of the liquid formulation), and most preferably from about 0.01% (by total weight of the liquid formulation) to about 10% (by total weight of the liquid formulation).

In another embodiment of the present invention, an agent capable of decreasing the activity of the enzyme ceramidase is introduced into or onto a personal care product to improve the health of skin contacted by the personal care product by maintaining or increasing the amount of intracellular and extracellular ceramides. As mentioned above, ceramidase is an enzyme that can destroy ceramides. Although ceramidase, which is naturally present in skin, performs a valuable, necessary function in some layers of the skin, ceramidases introduced onto the skin's surface or into the upper layers of the skin from external sources, such as bacterial ceramidases, which can be present in fecal matter, for example, can destroy ceramides and lead to various skin problems as discussed above. As used herein, the phrase "decreasing the activity of the enzyme ceramidase" means that the enzymatic activity of ceramidase is decreased in the presence of the agent as compared to the enzymatic activity of ceramidase in the absence of the agent. By introducing the agents described herein into or onto a personal care product, the agent contacts the skin during use and can interact with ceramidases deposited thereon and reduce the enzymatic activity of the ceramidases. This results in a decrease in destruction of the ceramides.

The agent, or combination of agents, introduced into or onto the personal care product preferably reduces the enzymatic activity of ceramidase by at least about 50%, more preferably at least about 75%, and most preferably at least about 90% as compared to the ceramidase activity in the absence of the agent. In one embodiment, the agent or combination of agents, introduced into or onto the personal care product preferably reduces the enzymatic activity of ceramidase by at least about 50%, more preferably at least about 75%, and most preferably at least about 90% as compared to the ceramidase activity in the absence of the agent as determined by a CAST Ceramidase Activity Screening Test set forth herein. The ceramidase activity reducing agent is preferably for decreasing ceramidase activity by at least about 50% as noted above. While this is the purpose and capability of the agent under many circumstances, it is noted that under certain conditions of application and skin condition, the actual decrease in activity experienced on the skin may be other than at least about 50% even though the agent is for decreasing such activity by at least about 50%.

CAST Ceramidase Activity Screening Test

Agents, such as botanical extracts and related compounds, for example, are tested for their ability to decrease the activity of ceramidase in a ceramidase/ceramide system. A decrease in the activity of ceramidase results in an increase in the level of ceramides. The Ceramidase Activity Screening Test is completed as follows:

Preparation of Testing Solutions:

Step 1: Preparation of Testing Solution Comprising Ceramidase (Fecal Extract), Agent, and Ceramide: Combine the following to prepare a 100 microliter test solution: (1) 10 microliters of agent where the agent is an aqueous solution or oil (if the agent is a powder solid, prepare 10 microliters of a 0.1 microgram/milliliter solution by dissolving the appropriate amount of powder or solid in Phosphate Buffered Saline, pH=7.4); (2) 10 microliters of infant fecal extract in Phosphate Buffered Saline, pH=7.4 prepared by extracting 1 gram of infant feces in 9 mL of Phosphate Buffered Saline, pH=7.4, and vortexing the extraction for about 2 minutes followed by centrifugation to remove any solids; (3) 10 microliters of 250 microgram/milliliter C5 ceramide in Phosphate Buffered Saline, pH=7.4; and (4) 70 microliters of Phosphate Buffered Saline, pH=7.4.

Step 2: Preparation of Control Testing Solution Comprising Ceramidase and Ceramide: Combine the following to prepare a 100 microliter test solution: (1) 10 microliters of infant fecal extract in Phosphate Buffered Saline, pH=7.4; (2) 10 microliters of 250 microgram/milliliter BIODIPY FL C5 ceramide (Molecular Probes, Eugene, Wash.) in Phosphate Buffered Saline, pH=7.4; and (3) 80 microliters of Phosphate Buffered Saline, pH=7.4.

Step 3: Preparation of Control Testing Solution Comprising Ceramide Combine the following to prepare a 100 microliter test solution: (1) 10 microliters of 250 microgram/milliliter BIODIPY FL C5 ceramide in Phosphate Buffered Saline, pH=7.4; and (2) 90 microliters of Phosphate Buffered Saline, pH=7.4.

Assay:

Step 1: Allow each testing solution to remain static at 25° C. for 18 hours to allow interaction and reaction between the Testing Solution components.

Step 2: Add 200 microliters of a 2:1 (by volume) mixture of chloroform:methanol to each testing solution to stop the chemical reactions. After the addition of the chloroform: methanol mixture, each of the testing solutions is vortexed for a period of about 1 minute to ensure that the chloroform: methanol mixture is thoroughly distributed throughout the testing mixture.

Step 3: Remove 0.8 milliliters of solution from the organic phase of each testing solution and introduce the removed solution into a thin layer chromatography vial for further analysis.

Thin Layer Chromatography Procedure:

Step 1: Introduce 10 microliters of a testing solution onto a thin layer chromatography plate, such as a high performance thin layer chromatography silica gel 60 plate as described above.

Step 2: Develop each testing solution by introducing a 90:20:0.5 (by volume) chloroform:methanol:ammonium hydroxide mixture onto each plate and allowing the mixture to run to a length of 8 centimeters.

Step 3: Illuminate each plate with a 364 nanometer light source and take pictures with a suitable camera, such as a digital Kodak DC 40. The digital image is transferred as a TIFF file to the Alpha Innotech Flourchem Plate Imaging System and analyzed as described above with similar positive (substrate and ceramidase) and negative (substrate and no enzyme) controls. A value above 1 indicates a ceramidase enhancer and a value below 1 indicates an inhibitor.

Suitable agents for use in combination with the personal care products described herein to decrease the activity of ceramidase by at least about 50% to ultimately maintain or increase the amount of ceramides in the skin include both botanical extracts and other compounds. Specifically, it has been found that the following agents decrease ceramidase activity as determined by the Ceramidase Activity Screening Test described herein by at least about 50% and are suitable for use in accordance with the present invention: Dragoderm, Ceramide Complex CLR (P), Green Tea HS-Chilowt, Comfrey Leaves Extract, Hydrolyzed Soy Protein, Glycoderm, Aloe Gel 1:1 Decolorized, American Ginseng, Aloe Ferox HS, and Phytoplenolin.

When present on a dry wipe substrate or on an absorbent product, the agent for decreasing the activity of ceramidase is present in an amount of from about 0.01% (by weight of the treated substrate or product) to about 50% (by weight of the treated substrate or product), preferably from about 0.01% (by weight of the treated substrate or product) to about 10% (by weight of the treated substrate or product). When present as part of the liquid formulation of a wet wipe, the agent is present in an amount of from about 0.01% (by total weight of the liquid formulation) to about 50% (by total weight of the liquid formulation), more preferably from about 0.01% (by total weight of the liquid formulation) to about 10% (by total weight of the liquid formulation).

Without being bound to a particular theory, it appears that the agents described herein for reducing the activity of the enzyme ceramidase accomplish this in one of two ways, or through a combination of both. First, the agents may actually be downregulating the production of ceramidase from the external source, which may be bacteria. By interacting with the bacteria and downregulating, or turning off or reducing ceramidase production, the amount of ceramides destroyed by the ceramidase enzyme is reduced as the concentration of ceramidase is decreased. Alternatively, or in combination with downregulation, the agent(s) may be chemically interacting with the ceramidase molecules and blocking or binding one or more active sites on the enzyme such that the ceramidase is no longer capable, or at least much less capable, of reacting with and destroying ceramides. Although this mechanism alone does not reduce the overall concentration of ceramidase on or near the skin's surface, it does effectively prevent the destruction of ceramides by reducing the ceramidase activity.

In an alternative embodiment of the present invention, a single agent can be introduced into or onto a personal care product to produce a dual effect; that is, the agent acts to increase sphingomyelinase activity and decrease ceramidase activity simultaneously. For example, Dragoderm has been shown to increase sphingomyelinase activity by more than 300% as determined by the SAST Sphingomyelinase Activity Screening Test set forth herein and has also been shown to decrease ceramidase activity by at least about 90% as determined by the CAST Ceramidase Activity Screening Test set forth herein. As such, when Dragoderm is introduced into or onto a personal care product, it produces the dual effect of not only increasing sphingomyelinase activity on the skin to ultimately produce an increased level of ceramides, but also decreases the destruction of ceramides on the skin by decreasing the activity of ceramidase. Thus, Dragoderm provides a dual benefit which is highly desirable. Along with Dragoderm, Aloe Ferox HS, American Ginseng, and Phytophenolin have been shown to not only increase sphingomyelinase activity, but also decrease ceramidase activity.

In a further embodiment of the present invention, a combination of agents can be utilized to produce the dual effect of increasing sphingomyelinase activity while decreasing ceramidase activity to produce an increased level of ceramides in the skin for improved skin health. For example, one agent capable of increasing sphingomyelinase activity can be used in combination with a second agent capable of decreasing ceramidase activity. Preferably, in order not to decrease the overall effectiveness of the combination of agents, the agent utilized to increase sphingomyelinase activity would not also significantly increase ceramidase activity and the agent utilized to decrease ceramidase activity would not significantly decrease sphingomyelinase activity. In one embodiment, for example, Chlorella, which has been shown to increase sphingomyelinase activity by more than about 400% based on the SAST Sphingomyelinase Activity Screening Test and has been shown to have no effect on ceramidase activity based on the CAST Ceramidase Activity Screening Test could be combined with Ceramide Complex CLR, which has been shown to decrease ceramidase activity by more than about 90% based on the CAST Ceramidase Activity Screening Test while not significantly effecting sphingomyelinase activity based on the SAST Sphingomyelinase Activity Screening Test.

In a still further embodiment of the present invention, the agents described herein for increasing the activity of sphingomyelinase or decreasing the activity of ceramidase can be utilized in combination with an organic or inorganic cofactor which is also capable of increasing the activity of sphingomyelinase to produce an increased amount of ceramides. Examples of suitable organic cofactors for use in combination with the agents described herein for increasing the activity of sphingomyelinase include reduced glutathione and yeast extracts such as *Schizosaccharomyces, Lipomyces,* and *Saccharomyces*. Suitable inorganic cofactors include magnesium. When present on a dry wipe substrate or on an absorbent product in combination with an agent capable of increasing the activity of sphingomyelinase, the cofactor is present in an amount of from about 0.01% (by weight of the treated substrate or product) to about 10% (by weight of the treated substrate or product), preferably from about 0.01% (by weight of the treated substrate or product) to about 1% (by weight of the treated substrate or product). When present as part of the liquid formulation of a wet wipe in combination with an agent capable of increasing the activity of sphingomyelinase, the cofactor is present in an amount of from about 0.01% (by total weight of the liquid formulation) to about 10% (by total weight of the liquid formulation), more preferably from about 0.01% (by total weight of the liquid formulation) to about 1% (by total weight of the liquid formulation).

The present invention is illustrated by the following example which is merely for the purpose of illustration and is not to be regarded as limiting the scope of the invention or manner in which it may be practiced.

EXAMPLE 1

In this Example, botanical extracts and other compounds were tested to determine what effect each compound had on sphingomyelinase activity according to the Sphingomyelinase Activity Screening Test set forth herein and on ceramidase activity according to the Ceramidase Activity Screening Test set forth herein.

Each of the compounds tested, the company where the compound was purchased, the product number of the compound, and the physical form of the compound are set forth in Table 1.

TABLE 1

| Compound | Company | Product Number | Physical Form |
|---|---|---|---|
| Sedaplant Richter | Chemisches Laboratorium, Berlin | 732384 | Aqueous |
| *Chlorella* | Bio-botanica, Hauppauge, NY | 951289 | Aqueous |
| Hexaplant Richter | Chemisches Laboratorium, Berlin | 732431 | Aqueous |
| Lavender | Gattefosse, Cedex, France | 21189 | Aqueous |
| Marigold (*Calendula*) | Bell Flavors & Fragrances, Inc. Northbrook, Illinois | 62565 | Aqueous |
| Gotu Kola PE 4:1 | Bio-botanica, Hauppauge, NY | 980657 | Powder |
| *Spirulina* | Bio-botanica, Hauppauge, NY | 951288 | Aqueous |
| Chamonile CL | Dragoco, Totowa, NJ | 2/033026 | Aqueous |
| *Harpagophytum* (Devil's Claw) | Indena-International Sourcing, Uppersaddle River, NJ | EG522 | Aqueous |
| Dragoderm | Dragoco, Totowa NJ | 1012550 | Aqueous |
| Phytoplenolin | Bio-botanica, Hauppauge, NY | 980510 | Aqueous |
| *Aloe* Ferox HS | Alban Muller International, Northvale, NJ | 7114158 | Oil |
| Sea Parsley Extract | Phillip Rocklel | R10418 | Aqueous |
| Butcher's Broom HS | Alban Muller International, Northvale, NJ | 8025951 | Aqueous |
| American Ginseng | Bio-botanica, Hauppauge, NY | 9865 | Aqueous |
| Microat afa Complex | Nurture Inc. Missoula, MT | 970512-06 | Aqueous |
| Actiphyte of Japanese Green Tea Conc. | Active Organics, Dallas, Tx | 300230-94 | Liquid |
| Arnica Oil CLR | Chemisches Laboratorium, Berlin | 732407 | Oil |
| Brazil Nut Oil | Croda, Parsippany, NJ | BR2-1004 | Oil |
| Safflower Oil | Arista Industries, Darien, Ct | 33767 | Oil |
| Olive Oil | Croda, Parsippany, NJ | OL2-175 | Oil |
| Evening Primrose Oil | Croda, Parsippany, NJ | IPH1-1059 | Oil |
| Ceramide Complex CLR (P) | Chemisches Laboratorium, Berlin | 732207 | Aqueous |
| Carrot Oil CLR | Chemisches Laboratorium, Berlin | 832526 | Oil |
| *Calundula* Oil CLR | Chemisches Laboratorium, Berlin | 832622 | Oil |
| Apricot Kernel Oil | Croda, Parsippany, NJ | AP-167 | Oil |
| St. John's Wort Oil CLR | Chemisches Laboratorium, Berlin | 732208 | Oil |
| Green Tea HS-Chilowt | Alban Muller, Montreuil Cedex, France | 12373-00 | Aqueous |
| Biodynes TRF (Yeast Extract) | Brooks Industries, South Plainfield, NJ | 39656 | Aqueous |
| Comfrey Leaves Extract | Bell Flavors & Frangrance, Northbrook, Il. | Req: 062565 | Aqueous |
| *Aloe* Gel 1:1 decolorized | Tri-K Industries, Northvale, NJ | | Aqueous |
| D1-alpha-Tocophenyl Acetate | Rocke Chem. | | Aqueous |
| Borage Oil | Arista Industries, Darien, CT | | Oil |
| Hydrolyzed Soy Protein | Croda, Parsippany, NJ | Hydrosoy 2000SA | Aqueous |
| MPC-Milk Peptide Complex | Chemisches Laboratorium, Berlin | 832641 | Powder |
| Hydrolyzed Whole Oats | Croda, Parsippany, NJ | Cromoist O-25 | Aqueous |
| Hydrolyzed Elastin | Croda, Parsippany, NJ | Crolastin | Aqueous |
| MAP, Potassium Laureth Phosphate, (0.2% in PBS) | Rhodia, Cranbury, NJ | | Aqueous |

TABLE 1-continued

| Compound | Company | Product Number | Physical Form |
|---|---|---|---|
| Mackeleen EN-77, Sunflower Seedaminopropyl Morpholine Lactate, (0.25% in PBS) | Mcintyre Group, University Park, Il. | EN-77 | Aqueous |
| Tween 20 (0.1% in PBS) | Sigma Chemical, St. Louis, Mo | | Aqueous |
| Sunflower Oil | Croda, Parsippany, NJ | SN2-104 | Oil |
| Avocado Oil CLR | Chemisches Laboratorium, Berlin | 832601 | Oil |
| Glycoderm | CLR Chemisches Laboratorium, Berlin, Germany | GLYCODERM (P) | Aqueous |

Sphingomyelinase Activity Screening Test

Each of the above-noted compounds was tested for its ability to increase the activity of sphingomyelinase. Each compound was prepared as a testing solution in the same manner as set forth herein.

Step 1: Preparation of Testing Solution Comprising Sphingomyelinase, Sphingomyelin, and Test Compound: A 100 microliter test solution was prepared by combining the following: (1) 10 microliters of test compound (if test compound was a powder, a 10 microliter solution of a 0.1 microgram/milliliter solution was prepared by dissolving the appropriate amount of powder in Phosphate Buffered Saline, pH=7.4 (VWR, Wet Chester, Pa.); (2) 10 microliters of a 0.1 microgram/milliliter sphingomyelinase (Sigma Chemical, St. Louis, Mo.) in Phosphate Buffered Saline, pH=7.4, solution; (3) 10 microliters of a 250 microgram/milliliter BODIPY C5 Sphingomyelin (Bodipy FL C5 Sphingomyelin, Molecular Probes, Eugene Or.) in Phosphate Buffered Saline, pH=7.4, solution; and (4) 70 microliters of Phosphate Buffered Saline, pH=7.4.

Step 2: Preparation of Control Testing Solution Comprising Sphingomyelinase and Sphingomyelin: A 100 microliter test solution was prepared by combining the following: (1) 10 microliters of a 0.1 microgram/milliliter sphingomyelinase in Phosphate Buffered Saline, pH=7.4, solution; (2) 10 microliters of a 250 microgram/milliliter BODIPY FL C5 Sphingomyelin in Phosphate Buffered Saline, pH=7.4, solution; and (3) 80 microliters of Phosphate Buffered Saline, pH=7.4.

Step 3: Preparation of Control Testing Solution Comprising Sphingomyelin: A 100 microliter test solution was prepared by combining the following: (1) 10 microliters of a 250 microgram/milliliter BODIPY FL C5 Sphingomyelin in Phosphate Buffered Saline, pH=7.4, solution; and (2) 90 microliters of Phosphate Buffered Saline, pH=7.4.

Step 4: Preparation of Control Testing Solution Comprising Test Compound and Sphingomyelin: A 100 microliter test solution was prepared by combining the following: (1) 10 microliters of test compound (if test compound was a powder, a 10 microliter solution of a 0.1 microgram/milliliter solution was prepared by dissolving the appropriate amount of powder in Phosphate Buffered Saline, pH=7.4 (2) 10 microliters of a 250 microgram/milliliter BODIPY FL C5 Sphingomyelin in Phosphate Buffered Saline, pH=7.4, solution; and (3) 80 microliters of Phosphate Buffered Saline, pH=7.4.

Assay:

Step 1: Each test solution was shaken for 30 minutes on a laboratory shaker at 25° C. to thoroughly mix each testing solution and allow chemical interaction and reaction between the testing mixture components.

Step 2: 1 milliliter of a 2:1 (by volume) mixture of chloroform:methanol was added to each testing solution to stop the chemical reactions. After the addition of the chloroform:methanol mixture, each of the testing solution was vortexed for a period of time of about 1 minute to ensure that the chloroform:methanol mixture was thoroughly distributed throughout the testing mixture.

Step 3: 0.8 milliliters of solution was removed from the organic phase of each testing solution and introduced into a thin layer chromatography vial for further analysis.

Thin Layer Chromatography Procedure:

Step 1: 5 microliters of a testing solution was introduced onto a thin layer chromatography silica gel 60 plate (MERCK, Damstady, Germany). The spotting of the testing solution was done with a CAMAG Auto TLC Sampler 4 (Muttenz, Switzerland).

Step 2: Each testing solution was developed by introducing a 90:20:0.5 (by volume) chloroform:methanol:ammonium hydroxide mixture onto each plate and allowing the mixture to run to a length of 8 centimeters.

Step 3: Each band was quantified with an Alpha Innotech Flourchem Plate Imaging System (San Leandro, Calif.). Each plate contained a maximum of ten testing samples including three positive control samples and one negative control sample. The plates were imaged by illuminating with a UV light source (364 nm) and a digital image was taken through a 585 nm barrier filter with the Flourchem Imager. All fluorescent bands were analyzed using the Flourchem image analysis software and the brightness for each band determined. The Flourchem software determined the Integrated Density Value (IDV) and the Area (pixels) for each fluorescent band. Brightness was then determined from these values. To calculate the effect of the compounds on enzyme activity, the negative control brightness was first subtracted from all of the samples. Then the test compound band on a plate was divided by the average value of the three positive control bands for the same plate. A value above 1 indicates a sphingomyelinase enhancer and a value below 1 indicates an inhibitor.

Ceramidase Activity Screening Test

Each of the above-noted compounds was also tested for its ability to decrease the activity of ceramidase. Each compound was prepared as a testing solution in the same manner as set forth herein.

Preparation of Testing Solutions:

Step 1: Preparation of Testing Solution Comprising Ceramidase (Fecal Extract), Agent, and Ceramide: A 100 microliter test solution was prepared by combining the following: (1) 10 microliters of test compound (if test compound was a powder, 10 microliters of a 0.1 microgram/milliliter solution was prepared by dissolving the appropriate amount of solid in Phosphate Buffered Saline, pH=7.4); (2) 10 microliters of infant fecal extract in Phosphate Buffered Saline, pH=7.4; (3) 10 microliters of 250 microgram/milliliter C5 ceramide in Phosphate Buffered Saline, pH=7.4; and (4) 70 microliters of Phosphate Buffered Saline, pH=7.4.

Step 2: Preparation of Control Testing Solution Comprising Ceramidase and Ceramide: A 100 microliter test solution was prepared by combining the following: (1) 10 microliters of infant fecal extract in Phosphate Buffered Saline, pH=7.4; (2) 10 microliters of 250 microgram/milliliter C5 ceramide in Phosphate Buffered Saline, pH=7.4; and (3) 80 microliters of Phosphate Buffered Saline, pH=7.4.

Step 3: Preparation of Control Testing Solution Comprising Ceramide: A 100 microliter test solution was prepared by combining the following: (1) 10 microliters of 250 microgram/milliliter C5 ceramide in Phosphate Buffered Saline, pH=7.4; and (2) 90 microliters of Phosphate Buffered Saline, pH=7.4.

Assay:

Step 1: Each testing solution was allowed to remain static at 25° C. for 18 hours to allow interaction and reaction between the Testing Solution components.

Step 2: 200 microliters of a 2:1 (by volume) mixture of chloroform:methanol was added to each testing solution to stop the chemical reactions. After the addition of the chloroform:methanol mixture, each of the testing solutions was vortexed for a period of time of 1 minute to ensure that the chloroform:methanol mixture was thoroughly distributed throughout the testing mixture.

Step 3: 0.8 milliliters of solution was removed from the organic phase of each testing solution and introduce the removed solution into a thin layer chromatography vial for further analysis.

Thin Layer Chromatography Procedure:

Step 1: 10 microliters of a testing solution was introduced onto a high performance thin layer chromatography silica gel 60 plate.

Step 2: Each testing solution was developed by introducing a 90:20:0.5 (by volume) chloroform:methanol:ammonium hydroxide mixture onto each plate and allowing the mixture to run to a length of 8 centimeters.

Step 3: Each band was quantified with an Alph Innotech Flourchem Plate Imaging System (or similar system) as discussed above.

The results of these experiments are set forth in Table 2.

TABLE 2

| Compound | Effect on Sphingomyelinase Activity | Effect on Ceramidase Activity |
| --- | --- | --- |
| Sedeplant Richter | 7.6 Times Activity | ≧1 Times Activity |
| Chlorella | 7.1 Times Activity | No Effect |
| Hexaplant Richter | 6.6 Times Activity | ≧1 Times Activity |
| Lavender | 6.4 Times Activity | No Effect |
| Marigold (Calendula) | 6.4 Times Activity | ≧1 Times Activity |
| Gotu Kola PE 4:1 | 6.2 Times Activity | ≧1 Times Activity |
| Spirulina | 5.7 Times Activity | No Effect |
| Chamonile CL | 5.1 Times Activity | ≧1 Times Activity |
| Harpagophytum (Devil's Claw) | 4.9 Times Activity | ≧1 Times Activity |
| Dragoderm | 4.5 Times Activity | ≦0.1 Times Activity |
| Phytoplenolin | 4.3 Times Activity | ≦0.5 Times Activity |
| Aloe Ferox HS | 4.1 Times Activity | ≦0.5 Times Activity |
| Sea Parsley Extract | 3.4 Times Activity | No Effect |
| Butcher's Broom HS | 3.4 Times Activity | ≧1 Times Activity |
| American Ginseng | 3.2 Times Activity | ≦0.5 Times Activity |
| Microat afa Complex | 3.1 Times Activity | ≧1 Times Activity |
| Actiphyte of Japanese Green Tea Conc. | 2.4 Times Activity | ≧1 Times Activity |
| Arnica Oil CLR | 1.8 Times Activity | ≧1 Times Activity |
| Brazil Nut Oil | 1.5 Times Activity | ≧1 Times Activity |
| Safflower Oil | No Effect | ≧1 Times Activity |
| Olive Oil | No Effect | ≧1 Times Activity |
| Evening Primrose Oil | No Effect | ≧1 Times Activity |
| Ceramide Complex CLR (P) | No Effect | ≦0.1 Times Activity |
| Carrot Oil CLR | No Effect | ≧1 Times Activity |
| Calundula Oil CLR | No Effect | ≧1 Times Activity |
| Apricot Kernel Oil | No Effect | ≧1 Times Activity |
| St. John's Wort Oil CLR | No Effect | ≧1 Times Activity |
| Green Tea HS-Chilowt | 0.8 Times Activity | ≦0.1 Times Activity |
| Biodynes TRF (Yeast Extract) | 0.8 Times Activity | No Effect |
| Comfrey Leaves Extract | 0.7 Times Activity | ≦0.1 Times Activity |
| Aloe Gel 1:1 decolorized | 0.7 Times Activity | ≦0.5 Times Activity |
| D1-alpha-Tocophenyl Acetate | 0.6 Times Activity | ≧1 Times Activity |
| Borage Oil | 0.6 Times Activity | ≧1 Times Activity |
| Hydrolyzed Soy Protein | 0.6 Times Activity | ≦0.1 Times Activity |
| MPC-Milk Peptide Complex | 0.4 Times Activity | No Effect |
| Hydrolyzed Whole Oats | 0.3 Times Activity | ≧1 Times Activity |
| Hydrolyzed Elastin | 0.2 Times Activity | No Effect |
| MAP, Potassium Laureth Phosphate, (0.2% in PBS) | 0.1 Times Activity | No Effect |
| Mackeleen EN-77, Sunflower Seedaminopropyl Morpholine Lactate, (0.25% in PBS) | 0.1 Times Activity | No Effect |
| Tween 20 (0.1% in PBS) | 0.1 Times Activity | No Effect |
| Sunflower Oil | No Effect | ≧1 Times Activity |
| Avocado Oil CLR | No Effect | ≧1 Times Activity |
| Glycoderm | No Effect | ≦0.1 Times Activity |

As the data set forth in Table 2 indicate, several compounds tested exhibited the ability to increase sphingomyelinase activity and/or decrease ceramidase activity. Notably, Dragoderm, Phytoplenolin, Aloe Ferox HS, and American Ginseng are highly preferred agents as they all not only increase the activity of sphingomyelinase, but also decrease the activity of ceramidase.

In view of the above, it will be seen that the several objects of the invention are achieved. As various changes could be made in the above-described products and methods without departing from the scope of the invention, it is intended that all matter contained in the above description be interpreted as illustrative and not in a limiting sense.

What is claimed is:

1. A wipe comprising a fibrous wipe substrate, a liquid formulation, and an effective amount of sphingomyelinase activity increasing agent for increasing in vivo sphingomyelinase activity by at least about 100% as compared to the sphingomyelinase activity in the absence thereof, and an effective amount of a ceramidase activity decreasing agent for decreasing in vivo ceramidase activity by at least 50% as compared to the ceramidase activity in the absence thereof, wherein the sphingomyelinase activity increasing agent is selected from the group consisting of an aqueous extract of Lavender, an aqueous extract of Marigold (Calendula), an aqueous extract of Spirulina, an aqueous extract of Chamonile CL, an aqueous extract of Devil's Claw, an aqueous extract of intact Triticum vulgare wheat gluten, an aqueous extract of Sea Parsley, and an aqueous extract of American Ginseng; and wherein the ceramidase activity decreasing agent is selected from the group consisting of an aqueous extract of Triticum vulgare wheat gluten, an aqueous extract of Comfrey leaves, and an aqueous extract of Hydrolyzed Soy Protein.

2. The wet wipe as set forth in claim 1 wherein the sphingomyelinase activity increasing agent is present in an amount of from about 0.01% (by total weight of the liquid formulation) to about 50% (by total weight of the liquid formulation).

3. The wipe as set forth in claim 2 wherein the sphingomyelinase activity increasing agent is for increasing sphingomyelinase activity by at least about 100% as determined by a SAST Sphingomyelinase Activity Screening Test.

4. The wipe as set forth in claim 2 further comprising a cofactor selected from the group consisting of reduced glutathione, *Schizosaccharomyces, Lipomyces, Saccharomyces*, and magnesium.

5. The wet wipe as set forth in claim 2 wherein the sphingomyelinase activity increasing agent is present in an amount of from about 0.01% (by total weight of the liquid formulation) to about 10% (by total weight of the liquid formulation).

6. The wet wipe as set forth in claim 1 wherein the ceramidase activity decreasing agent is present in an amount of from about 0.01% (by total weight of the liquid formulation) to about 50% (by total weight of the liquid formulation).

7. The wipe as set forth in claim 6 wherein the ceramidase activity decreasing agent is for decreasing ceramidase activity by at least about 50% as determined by a CAST Ceramidase Activity Screening Test.

8. The wet wipe as set forth in claim 6 wherein the ceramidase activity decreasing agent is present in an amount of from about 0.01% (by total weight of the liquid formulation) to about 10% (by total weight of the liquid formulation).

9. A product for improving the skin health comprising an absorbent substrate and an effective amount of sphingomyelinase activity increasing agent for increasing in vivo sphingomyelinase activity by at least about 100% as compared to the sphingomyelinase activity in the absence thereof, and an effective amount of a ceramidase activity decreasing agent for decreasing in vivo ceramidase activity by at least 50% as compared to the ceramidase activity in the absence thereof, wherein the sphingomyelinase activity increasing agent is selected from the group consisting of an aqueous extract of Lavender, an aqueous extract of Marigold (Calendula), an aqueous extract of Spirulina, an aqueous extract of Chamonile CL, an aqueous extract of Devil's Claw, an aqueous extract of intact Triticum vulgare wheat gluten, an aqueous extract of Sea Parsley, and an aqueous extract of American Ginseng; and wherein the ceramidase activity decreasing agent is selected from the group consisting of an aqueous extract of Triticum vulgare wheat gluten, an aqueous extract of Comfrey leaves, and an aqueous extract of Hydrolyzed Soy Protein.

10. The product as set forth in claim 9 wherein the sphingomyelinase activity increasing agent is present in an amount of from about 0.01% (by weight of the treated product) to about 50% (by weight of the treated product).

11. The product as set forth in claim 9 wherein the product is selected from the group consisting of a diaper, training pants, adult incontinence garments, feminine napkins, paper towels, tampons, breast pads, interlabial pads, facial tissue, wound management products, and bath tissue.

12. The product as set forth in claim 9 further comprising a cofactor selected from the group consisting of reduced glutathione, *Schizosaccharomyces, Lipomyces, Saccharomyces*, and magnesium.

13. The product as set forth in claim 9 wherein the ceramidase activity decreasing agent is present in an amount of from about 0.01% (by weight of the treated substrate) to about 50% (by weight of the treated substrate).

14. The product as set forth in claim 9 wherein the sphingomyelinase activity increasing agent is for increasing sphingomyelinase activity by at least about 100% as determined by a SAST Sphingomyelinase Activity Screening Test and the ceramidase activity decreasing agent is for decreasing ceramidase activity by at least about 50% as determined by a CAST Ceramidase Activity Screening Test.

15. The product as set forth in claim 9 wherein the sphingomyelinase activity increasing agent is present in an amount of from about 0.01% (by total weight of the treated product) to about 10% (by total weight of the treated product).

16. The product as set forth in claim 9 wherein the ceramidase activity decreasing agent is present in an amount of from about 0.01% (by total weight of the treated product) to about 10% (by total weight of the treated product).

* * * * *